United States Patent [19]

Tara

[11] Patent Number: 5,171,567
[45] Date of Patent: Dec. 15, 1992

[54] METHOD FOR THE TREATMENT OF ATLL AND THE INHALANT FOR THE SAME

[75] Inventor: Mitsutoshi Tara, Kagoshima, Japan

[73] Assignee: Shionogi & Co., Ltd., Osaka, Japan; a part interest

[21] Appl. No.: 494,216

[22] Filed: Mar. 15, 1990

[30] Foreign Application Priority Data

Apr. 4, 1989 [JP] Japan .................................. 1-86320

[51] Int. Cl.$^5$ .............................................. A61K 45/02
[52] U.S. Cl. .................................. 424/85.5; 530/351; 424/85.4
[58] Field of Search .............................. 424/85.5, 85.4

[56] References Cited

U.S. PATENT DOCUMENTS

| | | | |
|---|---|---|---|
| 4,613,500 | 9/1986 | Suzuki et al. | 514/3 X |
| 4,659,570 | 4/1987 | Terano | 424/85.5 |
| 4,675,184 | 6/1987 | Hasegawa et al. | 424/85.4 |
| 4,851,219 | 7/1989 | Sherwin | 424/85.5 |
| 4,895,716 | 1/1990 | Goldstein et al. | 424/85.5 |
| 4,985,242 | 1/1991 | Sekine et al. | 424/85.4 |

FOREIGN PATENT DOCUMENTS 276120  7/1988  European Pat. Off.

OTHER PUBLICATIONS

Tamura et al. in *Cancer*, vol. 59, pp. 1059-1062 (1987).
English Abstract of presentation by Dr. Tara, at a medical conference. Japanese presentation published in *Rinsho to Kenkyuu*, vol. 68, pp. 2761 to 2765 (1991).
Medline Abstract No. 90065143, J. Nakayama et al., "Cutaneous Lesion of Adult T-Cell Lymphoma Treated Successfully With Local Hyperthermia..." & Nippon Hifuka Gakkai Zasshi, Jul. 1989, vol. 99, No. 8, pp. 907-914.
Biological Abstract No. 83120094, K. Tamura et al., "Recombinant Interferon Beta and Gamma in the Treatment of Adult T-Cell Leukemia" & Cancer, vol. 59, No. 6, 1987, pp. 1059-1062.

*Primary Examiner*—Howard E. Schain
*Attorney, Agent, or Firm*—Spencer, Frank & Schneider

[57] ABSTRACT

An improved method for treating or curing ATL, with lowered side effects, comprising administering an effective amount of interferon-γ to a mammalian species in need of such treatment via respiratory tract by inhalation, wherein recommended is that a single dose of said interferon-γ to human adults is 1,000,000 JRU to 6,000,000 JRU and the single dose is repeated at a frequency between once-a-week and twice-a-day.

6 Claims, No Drawings

METHOD FOR THE TREATMENT OF ATLL AND THE INHALANT FOR THE SAME

BACKGROUND OF THE INVENTION

1. Field of the Invention

The present invention provides new use of interferon-γ (hereafter referred to as INF-γ), in more particularly it relates to useful methods for the treatment of adult T cell leukemia/lymphoma (hereafter referred to as ATL), which is characterized by the new route of administration i.e., inhalation. This invention also provides pharmaceutical compositions, suitable for inhalation and for the purposes above.

2. Prior Art

ATL was first described as a specific clinical entity by Takatsuki et al. in 1976, which has occurred frequently in Japan, especially in southern Kyushu island area. The detection and isolation of human T-lymphotropic virus type-I (hereafter referred to as HTLV-I) by Gallo and his colleagues in 1979, and the discovery of the association of the HTLV-I with ATL are expected to shed new light on human cancer study. No effective drugs have been found, nor have there been established any effective methods of treatment for ATL. Therefore, the prognosis of ATL have been reported to be poor, with most patients dying within a year.

Since interferons have not only activities against various viruses but also activities against a variety of tumors, studies have been made for the treatment of ATL with intravenous administration of these. However, neither independent use of IFN nor even its use in combination with other drugs has produced satisfactory results.

BRIEF SUMMARY OF THE INVENTION

This invention relates to improved methods for administering IFN-γ in treating or curing ATL, which are very safe. More particularly, it relates to methods with lowered side effects characterized in that, in the treatment of ATL, 1,000,000 JRU to 6,000,000 JRU of aerosolized IFN-γ is repeatedly administered via respiratory tract by inhalation at twice-a-day to weekly intervals to a mammalian species, esp., human adults in need of such a treatment.

DESCRIPTION OF THE PREFERRED EMBODIMENT

In view of the above, the inventors made strenuous efforts and studies, as a result of which it was found that when IFN-γ is administered directly to the lungs of the mammal by means of inhalation, it becomes possible to very effectively treat ATL. We have therefore completed the invention.

The inhalant of this invention may be in a liquid form, or in a powder form, or in a crystal form. When in a liquid form, it can be supplied in ampules; and when in a powder or crystal form, it is packed in vials, which is, at the time of use, dissolved in distilled water for injection use or in physiological saline, and then administered with a nebulizer.

For the purpose of this invention, it is not particularly necessary to use any additive or the like. However, when the product is packed in vials, and it is to be used after being dissolved, it is desirable to add to the main ingredient, namely IFN-γ, serum albumin or a surfactant, and maltose and a buffer solution, when solubility, storage stability, etc. of IFN-γ are taken into consideration.

Such a preparation is made into a solution, and administered by inhalation with the use of a nebulizer. In so doing, it is not desirable for the solution of the preparation to be extremely acidic or alkaline. Therefore, when a buffer solution is used, such buffer should be used as keeps the solution practically in a neutral range. The thus prepared solution is very desirable as it seldom causes the inflammation, etc. at the administration site. In this invention, it is preferable to use phosphate buffer, and it is desirable for the buffer solution to show a buffer range of about pH 6.5–7.5.

Furthermore, to prevent inflammation or allergic reaction, pretreatment may be made, if necessary, with a steroid or the like. A steroid or the like may be added to the preparation beforehand. In addition, an antibiotic or the like can also be given parenterally or orally to prevent infection or for the purpose of treatment. It is also possible to add an aminoglucocide antibiotic, etc. to the solution for inhalation.

The solubility in water of polypeptide such as IFN-γ is low. So, for the inhalation of the therapeutically necessary amount of IFN-γ, a large amount of water is necessary, but this is not desirable for an inhalant. If the product is suspended in a small amount of water, the sprayed particles become large even with the use of a high-performance nebulizer, and consequently, it becomes difficult for the drug to reach the target site. This is not desirable. On the other hand, when serum albumin is added, the solubility and storage stability of IFN-γ are improved, with the result that the drug can be dissolved completely in the minimum amount of water or physiological saline solution. Then, the aforesaid drawbacks are all solved. The solution thus prepared shows an unexpectedly good solubility, and even when the solution is left for a long time at room temperature, no turbidity or the like takes place, and thus its stability is maintained. Nor was there seen any decrease in the potency of IFN-γ. As for serum albumin, human serum albumin is used preferably, and it can be substituted by a surfactant.

The IFN-γ used in this invention is that of natural origin or of recombinant type. What is especially preferable is recombinant human IFN-γ (hereafter referred to specifically as hIFN-γ).

The single dosage IFN-γ is about 1,000,000 to 6,000,000 JRU, preferably about 3,000,000 JRU, which is dissolved in about 5 to 30 ml of distilled water for injection use and/or physiological saline and then administered by inhalation over several minutes to several tens of minutes with using a nubulizer or the like. The inhalation is given at the frequency of once a week to once a day. For an inpatient, it is given more frequently. For an outpatient after remission, it is given once a week. Thus, the single dosage and the frequency to apply may vary, depending on the patient's symptoms or conditions.

The composition of this invention and the method of this invention are useful for even the single therapy of using IFN-γ alone. However, it may be also useful in combination with a conventional chemotherapy. It is recommendable to give this inhalation in combination with a publicly-known treatment by combined use of a plural number of drugs. When necessary, radiotherapy may also be used in combination with the inhalation.

An example of the preparation of this invention is given below:

| | |
|---|---|
| IFN-γ | About 1,000,000–6,000,000 JRU |
| Human serum albumin | About 0.2–40 mg |
| Maltose | About 0.02–0.4 g |
| L-cystein | About 0.1–2.0 mg |
| 0.1 M phosphate buffer | A necessary amount to make the whole 2.0 ml. |

When a freeze-dried preparation is desired, a solution consisting of the above ingredients is frozen quickly at −10° to −60° C., preferably at −25° to −40° C., for several minutes to 10 and several hours. After that, if necessary, the product is kept at about 0.005 to 1 mb for about 5 to 72 hours, while supplying heat of sublimation, and thereby water is removed by sublimation so as to bring the water content down to a desired level. Then, if necessary, inert gas such as nitrogen, or dried air may be supplied in the container, which is then closed tightly. In taking the foregoing procedures, it is desirable to use a conventional method. The freeze-dried product obtained as above is completely soluble in about 1 to 2 ml of distilled water.

The following Examples and Trials serve to illustrate the practical formulations and methods of the present invention, but those are not intended to limit the scope of this invention.

EXAMPLE

In a suitable quantity of 0.1M sodium dihydrogen phosphatedisodium monohydrogen phosphate buffer, the pH of which has been adjusted to 6.8, are dissolved $7.5 \times 10^8$ JRU equivalent of hIFN-γ, 1.25 g (as dry weight) of human serum albumin, 12.5 g (as dry weight) of maltose of pharmacopoeia grade, and 0.075 g of Lcystein. To this is added the aforesaid buffer solution to bring the total volume to 500 ml, which is then filtered through a suitable membrane filter, whereby a germ-free solution is obtained. The germ-free solution is supplied in vials at 2 ml per vial. The vials are then frozen at a temperature below −25° C., and while keeping the product at a temperature below −25° C., freeze-drying is performed by a conventional method, whereby a freeze-dried preparation is obtained.

Clinical Trials

Testing preparation

A vial of S-6810 (freeze-dried preparation, each containing 3,000,000 JRU of hIFN-γ) furnished by Shionogi & Co., Ltd. is dissolved in 1 ml of distilled water for injection use, which is then diluted with 20 ml of physiological saline solution. The solution thus prepared was administered to the following patients by inhalation over 20 minutes with the use of an ultrasonic nebulizer. Unless otherwise indicated, the inhalation was given once daily.

Patients receiving inhalation

The aforesaid treatment was given to 12 patients who had been finally diagnosed as having ATL. Of these 12 patients, 6 patients (Case Nos. 1–6: 4 chronic type and 2 acute type) received this inhalation therapy without any other chemotherapy, and 6 patients (Case Nos. 7–12: 3 acute type and 3 lymphoma type) received it together with combination chemotherapy. The combination chemotherapy regimen consisting of Cytarabine, Vincristine (or Vindesine), Cyclophosphamide, Prednisolone and Peplomycin are shown in Table.

Criteria for the evaluation of effect

The effect of the treatment was evaluated based on the criteria for the evaluation of effect in the chemotherapy of cancer set by Koyama-Saito group. A complete disappearance of detectable abnormalities was rated as CR (complete response), contraction rate of 50% or more as PR (partial response), contraction rate of less than 50% and enlarging rate of less than 25% as NC (no change), and enlarging rate of 25% or more as PD (progressive disease). Three patients (case 1, 4 and 5; 2 chronic type and 1 acute type) out of 6, treated with aerosolised IFN-γ inhalation therapy alone, obtained PR (effective rate, 50%). Four patients (case 7, 8, 10 and 12; 2 acute type and 2 lymphoma type) out of 6, treated with the combination of the aerosolised IFN-γ inhalation therapy and the chemotherapy, obtained PR (effective rate, 67%). The response might be judged as CR in these 7 patients if abnormal lymphoid cells (ATL-like cells) on examination of blood smears disappeared. The details of each patient are given below:

Case 1 (74 years old, female; chronic type)

This patient has a previous history of a chronic bronchitis-like respiratory disease for about 6 years. She has had fever, cough, sputum, and weight loss for these 2 months. Her doctor, pointed out hematological abnormalities and sent her to us for hospitalization. At the time of admission, there were no particular physical findings worthy of note. Her % VC was 81% and % $FEV_{1.0}$ was 56%.

From one month after hospitalization, inhalation therapy (once a day) was started on as a diagnosis of ATL. From about one month after the start of the inhalation, marked improvement was seen in hematological findings and surface marker analysis of peripheral blood lymphocytes, and at the same time, cough and sputum abated, body weight increased, and the fever tended to abate. Thus, marked improvement was observed in her general condition. She is still receiving the treatment at 3 to 4 times a week as outpatient and continues to show no evidence of recurrence.

Case 2 (59 years old male; chronic type)

This patient came to us for admission because of leucocytosis with abnormal lymphocytes (ATL cells), which was picked up during a complete health examination. There were nothing noteworthy in subjective or objective symptoms, or in physical findings. With a diagnosis of ATL 3,000,000 JRU of IFN-γ was given (once a day) by intramuscular injection for 54 days. After he was discharged from the hospital, he continued to come to hospital, twice a week, to receive the treatment. From 3 months before (8 months after he was first hospitalized), inhalation therapy was started at our outpatient clinic (3 to 4 times/week). No clear improvement in hematological findings was seen throughout the treatment periods. However, there are no particular subjective or objective symptoms even at present, and the patient is leading a normal life.

Case 3 (71 years old, male; chronic type)

This patient had had chronic bronchitis-like symptoms from time to time since a few years ago. When he was hospitalized for dysuria at the department of urology of our hospital, he was found to have a hematological abnormality, so he was transferred to our department. Then, he was found to have prostatic hypertrophy. At the same time, the chest X-ray view and pulmonary function test showed a diffuse pan-bronchiolitis-like abnormality. After hospitalization, inhalation therapy was started. During the hospitalization, he received inhalation every day for 50 days, and after discharge from the hospital, he continues to receive the treatment 3 times a week. No clear improvement was observed in hematological findings, and cough and sputum persisted. Therefore the effect was rated as NC.

Case 4 (56 years old, male; chronic type)

From 3 months before, the patient began to have dry cough, a slight fever, and weight loss (4 kg/3 months). He was diagnosed by his community doctor as having malignant lymphoma and aspergillosis of the lung, and the patient was admitted to our hospital for close examinations.

Generalized superficial lymph nodes swelling, up to the size of the tip of the thumb, were palpable, and rale was noticed in the left lung. The inhalation therapy was started on with oral administration of amphotericin B syrup and an penicillin type antibiotic as a diagnosis of ATL with aspergillosis of the lung. After start of the inhalation, the fever abated soon, and improvement was also seen in dry cough. After 2 months, the swelling of lymph nodes disappeared, OKT4/OKT8 ratio normalized, and the body weight was restored. Improvement was also observed in the abnormal shadow previously seen in the chest X-ray view. He continues to receive the therapy 3 times a week at our outpatient clinic.

Case 5 (52 years old, male; acute type)

The patient has had constipation and abdominal distention since 3 weeks ago. He was found, by his family doctor, to have swellings of the liver and spleen, and also leukocytosis. He was then admitted to our hospital with suspected leukemia. Initial laboratory data: WBC 40,700 (with 86.5% ATL cells); OKT4/OKT8 ratio 25.44; LDH 3,160 Wrob. U.; total bilirubin 5.2 (direct 2.7) mg/dl; and alkaline phosphatase 40.1 K.A.U.

Mild Chemotherapy was started under intensive supportive therapy as a diagnosis of ATL. However, a resistance was seen, and fever persisted, with the temperature staying at the level of 39° C. And there occurred a lymph node swelling of the size of a quail egg. Two months after hospitalization, when chemotherapy was suspended, inhalation therapy was started. Then, the lymph nodes swelling, hepatomegaly and splenomegaly were disappeared, and marked improvement was seen in all laboratory findings, too. OKT4/OKT8 ratio was also normalized.

No chemotherapy was made after the start of the inhalation therapy. However, subjective and objective symptoms have all disappeared, with the exception that there was seen only 5-10% abnormal lymphoid cells in the peripheral blood. He is now back to his job and having an inhalation of IFN-γ every day at his home.

Case 6 (61 years old, female; acute type)

This patient was admitted to our hospital because of left cervical lumph nodes swelling noticed from 1 month ago. At the time of admission, generalized superficial lymph node swellings, up to the size of a walnut, were palpable. The patient did not respond to any drug such as YK-176 (2'-deoxycoformycin <DCF>), MTX, or other combination chemotherapy. One month after every chemotherapy was suspended, when the underlying disease worsened, inhalation therapy was given every day without using any other chemotherapy. At one time, increase in LDH leveled off, and the swelling of lymph nodes tended to become smaller. However, abdominal lymph nodes swelling had become remarkable and died after the 6 month hospitalization.

Results on Cases 1 to 6 are summarized in Table 1 and those on Cases 7 to 12 are in Table 2.

Case 7 (38 years old, female; acute type)

This patient had had chronic bronchitis-like symptoms since 8 months ago, and was referred to our hospital because of painful right cervical lymph nodes swelling and abnormal chest X-ray observation. Physical examination revealed systemic lymph nodes swelling, up to 4 cm in diameter. In the generalized lung field could be heard rales. The liver and spleen were not palpated. She was diagnosed as malignant lymphoma, diffuse, pleomorphic type (T-cell type with markers of both CD4 and CD8).

She then was started on IFN-γ inhalation therapy with combination chemotherapy (modified VDS-CAP combination chemotherapy). One month after the treatment, lymph nodes swelling were markedly decreased in size, and improvement of chest Xp view was seen. She continues to receive the treatment in the outpatient clinic and is still in PR.

Case 8 (35 years old, female; acute type)

This patient was referred to our hospital because of generalized lymph nodes swelling, cough and skin rashes. Chest Xp revealed bilateral hilar lymph nodes swelling with diffuse abnormal shadows in the all lung field. Histological examination of a lymph node biopsy specimen showed malignant lymphoma, diffuse, medium-sized cell type (T-cell type with markers of CD4, CD11 and CD25).

As a diagnosis of ATL the IFN-γ inhalation therapy was started on with the combination chemotherapy with good effect. However, 6 weeks later she developed recurrence of the disease in the systemic lymph nodes with extensive skin rashes. The patient repeats recurrence and PR several times and still continues the inhalation therapy with other combination chemotherapy.

Case 9 (47 years old, female; acute type)

This patient was referred to our hospital from her community hospital. She had been admitted at the hospital because of pain in the knee and foot joints, which was more evident on gait. During evaluation she was found to have multiple osteolytic lesions and ATL cells on a film of the peripheral blood. A diagnosis of ATL was made and she was referred.

The IFN-γ inhalation therapy was started on with the combination chemotherapy without noticeable improvement.

Case 10 (55 years old, female; lymphoma type)

This patient was first admitted to our hospital with enlargement of submandibular, axillary and inguinal lymph nodes, the largest measuring 4.0 cm in diameter. Five weeks prior to her admission she had noticed a swelling on the left side of her submaxillary nodes. A biopsy of a inguinal node showed malignant lymphoma, diffuse, medium-sized cell type (T-cell type with markers of CD3, CD11 and CD25).

As a diagnosis of ATL she started to receive the IFN-γ inhalation therapy with the combination chemotherapy. Two weeks after the treatment, almost all the lymph nodes swelling was disappeared, but 1 to 3% of abnormal lymphoid cells (ATL-like cells) were seen on peripheral blood smears. She continued the inhalation therapy 3 times a week at her home, but 33 weeks after the treatment she developed recurrence of the disease in the neck. She was admitted again, and received the IFN-γ inhalation therapy twice-a-day with other combination chemotherapy with remarkable effect, and was discharged from our hospital in condition of PR. Now she continues the inhalation every day at her home.

Case 11 (49 years old, female; lymphoma type)

This patient was referred to our hospital because of skin rashes, cough, dyspnea, fever up, ATL cells on the examination of blood smear and extensive reticulogranular shadows in the bilateral lung field in chest Xp view.

As a diagnosis of ATL she started to receive the IFN-γ inhalation therapy with ordinaly conservative treatment including antibiotics. All the symptoms improved gradually by the treatment for 3 months, but lymph nodes swelling appeared in the neck. Histological examination of the specimen obtained by lymph node biopsy revealed malignant lymphoma, diffuse, medium-sized cell type (T-cell type with markers of CD4 and CD25). An additional combination chemotherapy was given with poor effect. She died due to sepsis 5 months after the treatment.

Case 12 (41 years old, male; lymphoma type)

This patient had been in his usual state of good health until 1 month prior to admission of his community hospital, when he noticed right cervical lymph nodes enlargement. At his community hospital, histological examination of the specimen obtained by right cervical lymph node biopsy revealed malignant lymphoma, diffuse, pleomorphic type (T-cell type with markers of CD3 and CD25), and chest Xp showed bilateral hilar lymph nodes swelling. Four weeks later, he was referred to our hospital for the treatment. The combination treatment of IFN-γ inhalation and chemotherapy was given successfully, and one month after the therapy, almost all symptoms disappeared. He continues to receive the same treatment at the outpatient clinic. No evidence of recurrence is seen.

TABLE 1

| Case No. | Risk | Conditions before treatment | | | Total dose of IFN-γ, × $10^8$ JRU | Effect and duration of effect | | Side effects |
|---|---|---|---|---|---|---|---|---|
| | | Performance status | WBC (ATL cell %) | Chemotherapy | | Effect | Duration (weeks) | |
| 1 | M | 1 | 8,800 (44.0%) | — | 201 | PR | 16+ | Mild fever |
| 2 | L | 0 | 8,700 (14.0%) | — | 144 | NC | 12+ | — |
| 3 | L | 1 | 12,300 (38.0%) | — | 186 | NC | 12+ | Mild fever |
| 4 | M | 0 | 6,700 (45.5%) | — | 108 | PR | 4+ | — |
| 5 | H | 4 | 3,600 (22.0%) | + | 237 | PR | 10+ | Mild fever |
| 6 | H | 3 | 6,900 (9.0%) | + | 66 | PD | — | — |

Remarks)
Performance status (PS) was graded based on the criteria set by WHO. Risk was classified into the following groups by the standard set by the Malignant Lymphoma Study Group: L: Low risk; M: Moderate risk; and H: High risk (J. Clin. Oncol., Vol. 6, No. 7 1088–1097 (1988)).

TABLE 2

| Case No. | Risk | Conditions before treatment | | | Total dose of IFN-γ, × $10^8$ JRU | Effect and duration of effect | | Side effects |
|---|---|---|---|---|---|---|---|---|
| | | Performance status | WBC (ATL cell %) | Chemotherapy | | Effect | Duration (weeks) | |
| 7 | M | 1 | 12,800 (30.0%) | — | 777 | PR | 34+ | — |
| 8 | H | 1 | 9,300 (23.5%) | — | 660 | PR | 6 | — |
| 9 | L | 1 | 4,100 (22.0%) | — | 120 | NC | 10 | — |
| 10 | H | 2 | 6,500 (0.0%) | — | 540 | PR | 31 | — |
| 11 | H | 4 | 8,300 (8.0%) | — | 315 | PD | — | — |
| 12 | M | 0 | 12,800 (0.0%) | — | 441 | PD | 19+ | — |

Remarks)
Performance status (PS) was graded based on the criteria set by WHO. Risk was classified into the following groups by the standard set by the Malignant Lymphoma Study Group: L: Low risk; M: Moderate risk; and H: High risk (J. Clin. Oncol., Vol. 6, No. 7 1088–1097 (1988)).

Conclusion

As compared with the conventional systemic administration of IFN-γ, this method of treatment is a more effective method, with very slight side effect. This method of treatment is considered to be useful not only for the treatment of ATL, but also widely for malignant tumors, refractory infections and AIDS.

What is claimed is:

1. A method for the treatment of ATL comprising administering an effective amount of interferon-γ to the lungs of a mammalian species suffering from ATL via respiratory tract inhalation.

2. The method claimed in claim 1, wherein 1,000,000 JRU to 6,000,000 JRU of said interferon-γ is administered from once-a-day to weekly intervals.

3. The method claimed in claim 2, wherein said interferon-γ is human interferon-γ.

4. The method claimed in claim 1, wherein said interferon-γ is recombinant interferon-γ.

5. The method claimed in claim 1, additionally comprising nebulizing an aqueous solution or suspension of said interferon-γ.

6. The method claimed in claim 1, wherein said interferon-γ is administered in conjunction with chemotherapy or radiotherapy.

* * * * *